US00PP36636P2

(12) United States Plant Patent
Hansen

(10) Patent No.: US PP36,636 P2
(45) Date of Patent: Apr. 29, 2025

(54) ***MANGAVE* PLANT NAMED 'Hope and a Prayer'**

(50) Latin Name: ***Manfreda* x *Agave* hybrid**
Varietal Denomination: Hope and a Prayer

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 31 days.

(21) Appl. No.: 18/445,828

(22) Filed: Feb. 23, 2024

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP31,274 P2 * 12/2019 Hansen ..... A01H 6/12
Plt./373

* cited by examiner

*Primary Examiner* — Karen M Redden
*Assistant Examiner* — Zachariah Allan Kay

(57) ABSTRACT

A new and unique X *Mangave* plant named 'Hope and a Prayer' characterized by habit that is a rounded mounded and becomes globose to pyriform-shaped with maturity. The numerous lanceolate leaves are dark, olive-green in the center and yellowish to chartreuse on the margin with small, widely-spaced, marginal teeth and apical mucro becoming wine-colored. Leaves develop small reddish-purple spots on adaxial and abaxial sides with high ultraviolet exposure. The new plant is suitable as a potted houseplant plant, as a container plant for the patio or garden and for the garden or planted in the landscape.

1 Drawing Sheet

Botanical classification: *Manfreda* x *Agave* hybrid.
Variety denomination: 'Hope and a Prayer'.

CROSS-REFERENCE TO RELATED APPLICATIONS

X *Mangave* plant named 'Living on a Prayer' U.S. Plant patent application Ser. No. 18/445,828.

STATEMENT REGARDING PRIOR DISCLOSURES UNDER 37 CFR 1.77(B)(6)

No plants of x *Mangave* 'Hope and a Prayer' have been sold, offered for sale, or disclosed in this country or anywhere in the world as of this filing.

BACKGROUND OF THE INVENTION

The present invention relates to the new and distinct X *Mangave* plant, X *Mangave* 'Hope and a Prayer' discovered on Mar. 13, 2023, by the inventor at a wholesale perennial nursery in Zeeland, Michigan, USA as a whole plant mutation of 'Praying Hands' U.S. Plant Pat. No. 34,508. Through trials at the same nursery the plant was referred to by the code 23-SP-MANG-1083. The new plant has been successfully asexually propagated initially by division of the pups in early 2024 and also in 2024 by shoot tip tissue culture at the same nursery in Zeeland, Michigan. This asexual propagation system has been found to produce stable and identical plants that maintain all the unique characteristics of the original plant in successive generations.

BRIEF SUMMARY OF THE INVENTION

X *Mangave* 'Hope and a Prayer' differs from its parents as well as all other *Manfreda, Agave* and x *Mangave* known to the applicant. The most similar x *Mangave* cultivars known to the inventor are: 'Pineapple Punch' U.S. Plant Pat. No. 32,041, 'Kaleidoscope' U.S. Plant Pat. No. 28,614, 'Aztec Treasure' U.S. Plant patent application Ser. No. 18/445,761, and 'Living on a Prayer' U.S. Plant Patent Application No. co-pending.

'Pineapple Punch' has foliage with a outwardly habit, apical mucro that are smaller and softer, leaves that are longer and a more strongly mahogany spotted, with marginal teeth that are softer and finer. 'Kaleidoscope' has longer more flexible foliage that is more arching, more finely marginally toothed with smaller apical mucro and a more heavily spotted with reddish-purple. 'Aztec Treasure' has a more outright and larger habit with larger and broader leaves having more intense purple spotting. 'Living on a Prayer' has a marbled variegation of white to whitish-green on a similar dark green leaf.

The parent, 'Praying Hands', lacks the yellowish-green marginal variegation on the foliage.

The new plant, 'Hope and a Prayer', is unique from all of these *Agave*, X *Mangave* and *Manfreda* known to the inventor by the following combined traits:

1. Rounded, mounded, with overall habit initially becoming globose to pyriform with maturity;
2. Foliage is lanceolate, slightly cupped distally, with small, short, marginal teeth, and long, stiff, apical mucro;

3. Leaves are dark olive-green in the center with a yellowish to chartreuse margin and the distal edge and teeth are reddish orange to wine-colored with wine-colored apical mucro;
4. Leaves develop small reddish-purple spots on adaxial and abaxial sides with high ultraviolet exposure;
5. Moderate growth rate.

BRIEF DESCRIPTION OF THE DRAWINGS

The photograph of the new plant demonstrates the overall appearance of 'Hope and a Prayer' including the unique traits as a one-year-old plant grown in greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
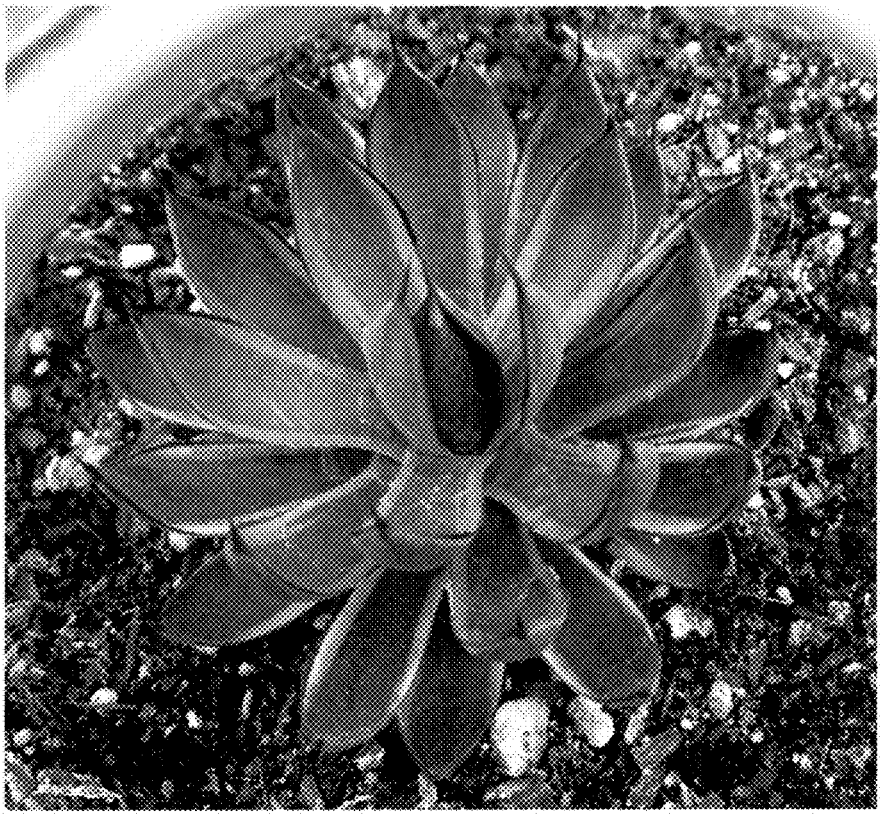
FIG. 1 shows the habit of the new plant from above.
Figure 2:
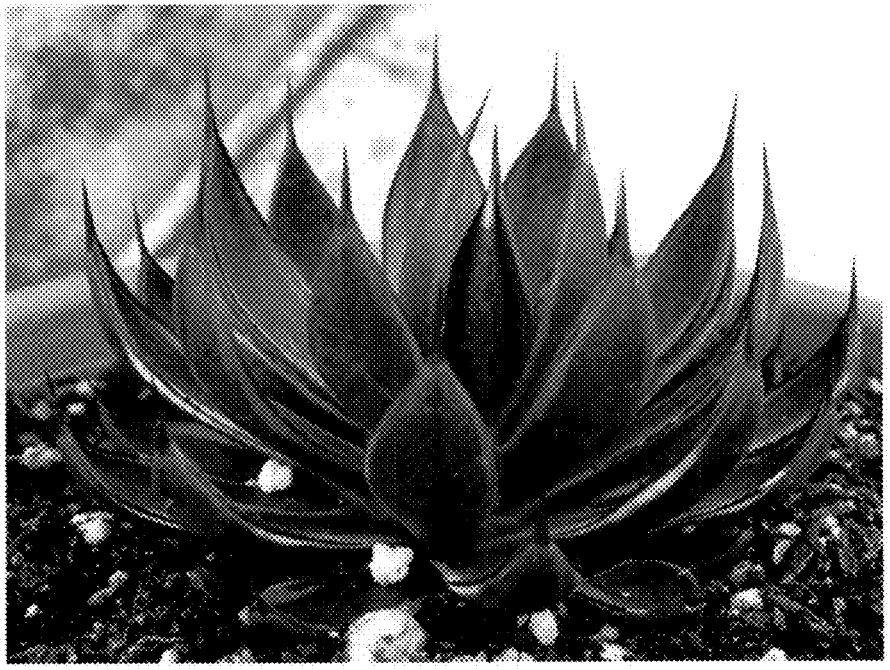
FIG. 2 shows the habit of the new plant from the side.

The following descriptions and color references are based on the 2015 edition of The Royal Horticultural Society Colour Chart except where common dictionary terms are used. The new plant, X *Mangave* 'Hope and a Prayer', has not been observed under all possible environments. The phenotype may vary slightly with different environmental conditions, such as temperature, light, fertility, moisture, and maturity levels, but without any change in the genotype. The following observations and size descriptions are of a one-year-old plant in a commercial wholesale greenhouse and in a greenhouse in Zeeland, Michigan with supplemental water and fertilizer as needed.

Botanical classification: x *Mangave* hybrid (*Manfreda* x *Agave*);

Parentage: 'Praying Hands';

Propagation: Sterile plant tissue culture;

Time to initiate roots from tissue culture: About 28 days;

Growth rate: Moderate;

Crop time: About 20 to 24 weeks to finish during lengthening spring days from an established 25mm tissue culture plug to a 65 mm diameter container;

Rooting habit: Fleshy, lightly branching, with roots up to 35 cm long and typically 3.0 mm diameter;

Root color: Nearest RHS 155D;

Plant shape and habit: Succulent herbaceous perennial with basal rosettes of about 29 fleshy leaves emerging outwardly from short stem and slightly arching upwardly and introrse toward apices, producing a symmetrical, rounded, globose, mound;

Plant size: Foliage height about 8 cm tall from soil line to the top of the leaves and 13.5 cm wide at about 6 cm above soil level;

Foliage description: Lanceolate; simple; sarcous; glabrous; fibrous; moderately lustrous adaxial and abaxial; margins smooth in distal two-thirds and dentate with small short teeth in proximal one-third; apex acute with long firm mucro; base truncate, sessile, clasping; flat surface; curved outwardly near base and upwardly and introrse toward apex; with yellowish-green marginal variegation up to 3 mm wide and an intermediate region between the margin and center up to 2 mm wide on the adaxial side, yellowish-green margin up to 2 mm wide on the abaxial side with no discernible intermediate region;

Leaf size: To about 8 cm long, about 2.2 cm wide in the widest portion about one-third from apex, basal portion flared to about 2 cm wide at attachment, and about 1.5 cm thick at base;

Marginal teeth: Flattened top to bottom; recurved toward leaf base; very small, about 0.5 mm long and 1 mm wide; proximally concentrated, to about 2 mm apart; distally void;

Foliage fragrance: None observed;

Leaf blade color:

*Adaxial*.—Young center between RHS 136A and RHS NN137A, the young margin nearest RHS 146D, and no discernible intermediate region.

*Abaxial*.—Young center between RHS 136A and RHS NN137A, the young margin nearest RHS 146B, and no discernible intermediate region.

*Adaxial*.—Mature center between RHS 136A and RHS, margin variable between RHS 146D and RHS 145A to between RHS 4C and RHS 151D, with intermediate region nearest RHS 147B.

*Abaxial*.—Mature center between RHS 136A and RHS NN137A, margin variable between RHS 146D and RHS 145A to between RHS 4C and RHS. 151D, with no discernible intermediate region. Spots of between 2 mm and 4 mm diameter between RHS N187B and RHS N186C develop on both adaxial and abaxial sides in high ultraviolet light exposure.

*Marginal teeth and edge color*.—Young adaxial and abaxial distally between RHS 172C and RHS 175B, proximally nearest RHS 146D, mature adaxial and abaxial distally nearest RHS 183A and proximally between RHS 4C and RHS 151D.

Mucro: Firm; sharp; straight, about 11 mm long and 2 mm across at base;

Mucro color: Young between RHS 172C and RHS 175B; mature between RHS N187A and RHS N186C;

Petiole: Sessile;

Veins: Parallel; not distinct;

Flower description: Flowers not yet observed;

Fruit: Not yet observed;

Seed: Not yet observed;

Disease resistance: x *Mangave* 'Hope and a Prayer' has not been observed to be resistant or susceptible to diseases common to other x *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental X *Mangave* plant named 'Hope and a Prayer' as herein described and illustrated.

* * * * *